United States Patent [19]

Bodoia

[11] Patent Number: 5,047,046
[45] Date of Patent: Sep. 10, 1991

[54] SURGICAL FORCEPS

[76] Inventor: Rodger D. Bodoia, 11341 17th NE, Seattle, Wash. 98125

[21] Appl. No.: 217,830

[22] Filed: Jul. 13, 1988

[51] Int. Cl.$^5$ .............................................. A61B 17/50
[52] U.S. Cl. .................................... 606/205; 606/210; 294/99.2
[58] Field of Search ...................... 128/321, 323, 354; 73/81, 85, 818, 862.54, 862.58; 81/318, 43, 483; 294/99.2; 606/205–208, 210, 211

[56] References Cited

U.S. PATENT DOCUMENTS

| | | | |
|---|---|---|---|
| 1,585,523 | 5/1986 | Barton | 128/323 |
| 2,010,493 | 8/1935 | Breck | 128/323 |
| 2,637,320 | 5/1953 | Greenberg . | |
| 3,665,925 | 5/1972 | Dersookian . | |
| 3,696,662 | 10/1972 | Foltz et al. . | |
| 3,785,381 | 1/1974 | Lower et al. . | |
| 3,818,784 | 6/1974 | McClure | 81/43 |
| 4,248,233 | 2/1981 | von Zeppelin et al. . | |
| 4,414,985 | 11/1983 | Myer . | |
| 4,467,678 | 8/1984 | Lindholm | 81/483 |

FOREIGN PATENT DOCUMENTS 2193141 2/1988 United Kingdom .

OTHER PUBLICATIONS

Alan B. Scott et al., "A Forceps to Measure Strabismus Forces", *Arch. Ophthal.*, vol. 88, Sep. 1972.

*Primary Examiner*—C. Fred Rosenbaum
*Assistant Examiner*—William W. Lewis
*Attorney, Agent, or Firm*—Gordon L. Peterson; Loyal M. Hanson

[57] ABSTRACT

A forceps includes elongated arms with proximal and distal sections, the distal sections extending to the forceps tips. The arms are arranged and interconnected to enable appositional movement of the tips in order to enable a user to grip an object between the tips and thereby apply a component of force to the object that is generally perpendicular to the direction of such appositional movement. The proximal and distal sections of the first arm are connected with a break-away joint that is arranged to quickly reduce the amount of coupling when the component of force being applied to the object exceeds a predetermined level. Joints enabling pivotal or linear movement of the distal sections relative to the proximal sections may be provided, spring-biased mechanical break-away components or strain-gauge-based electrical break-away components may be used, and a human sensible signal indicating when the force exceeds the predetermined level may be produced.

18 Claims, 3 Drawing Sheets

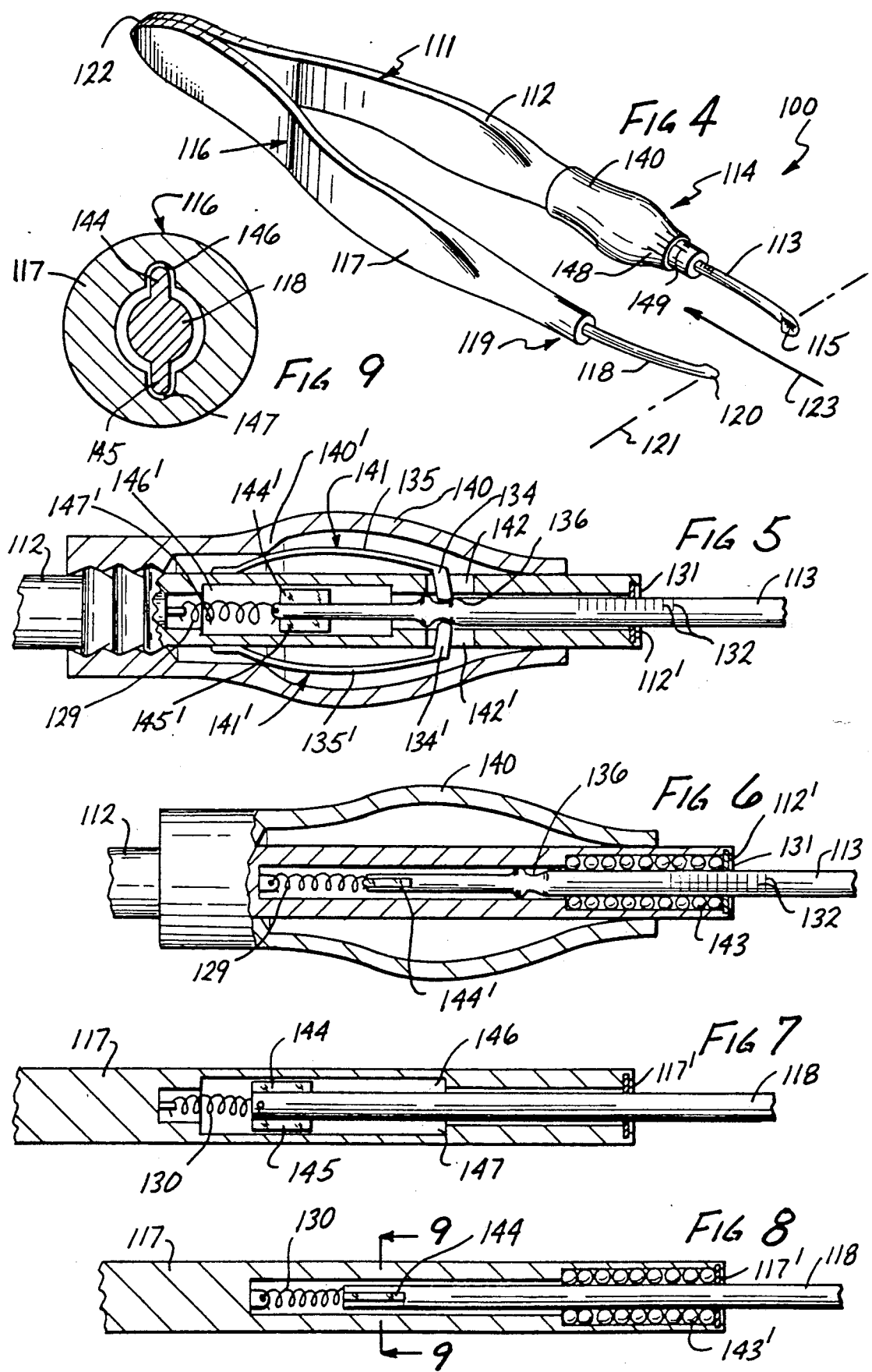

SURGICAL FORCEPS

BACKGROUND OF THE INVENTION

1. Technical Field

This invention relates generally to surgical instruments, and more particularly to a forceps.

2. Background Information

The surgeon uses a forceps to grasp, hold, and manipulate objects during various surgical procedures. Doing this with a properly designed forceps greatly facilitates such procedures, especially in such delicate work as tying sutures in the cornea following cataract surgery or corneal transplantation. This makes the details of forceps design particularly important.

In using a forceps for tying sutures during cataract and corneal surgery, for example, the surgeon may proceed with the aid of an operating microscope to manipulate a very small suture through very delicate tissue in the human eye. With great skill and utmost care, the surgeon then knots the suture and pulls on the knot to tighten it to a desired tension. Too much tension can tear the tissue or otherwise impair healing and too little tension may fail to retain the tissue in the desired position, allowing extrusion of intraocular contents, or entry of infectious organisms into the eye.

But despite the surgeon's skill and care, improper tension may be applied when manipulating a suture or other object with the forceps. Consequently, it is desirable to have some way to alleviate this concern.

SUMMARY OF THE INVENTION

This invention solves the problems outlined above with a surgical forceps having a break-away joint that operates to quickly reduce the force with which a suture is being pulled when the force increases beyond a predetermined level. This enables the surgeon to tighten a knot by pulling on the suture without concern that too much force will be applied.

Generally, a forceps constructed according to the invention includes first and second elongated arms, each of the arms having a proximal section and a distal section and each distal section having a tip. The arms are arranged and interconnected to enable appositional movement of the tips (toward and away from each other) in order to enable a user to grip an object between the tips and thereby apply a component of force to the object that is generally perpendicular to the direction of such appositional movement.

The proximal and distal sections of the first arm are connected with a first or break-away joint that couples the component of force to distal sections of the first arm. According to a major aspect of the invention, the first joint includes break-away means for quickly reducing the amount of coupling when the component of force being applied to the object exceeds a predetermined level.

According to another aspect of the invention, the first joint is arranged to enable relative movement of the proximal and distal sections and the break-away means includes detent means for restricting such relative movement until the component of force exceeds the predetermined value.

According to yet another aspect of the invention, the proximal and distal sections of the second arm are joined together with a second joint that enables relative movement of the proximal and distal sections of the second arm. The second joint is arranged to enable the distal section of the second arm to follow movement of the distal section of the first arm.

In one embodiment, the joints are arranged to enable the distal section of the first arm to move pivotally relative to the proximal section of the first arm. In another embodiment, they are arranged to enable the distal section of the first arm to move linearly relative to the proximal section of the first arm.

Yet another aspect of the invention includes means for indicating the relative magnitude of the component of force. This can be accomplished mechanically with a graduated scale, or electronically with a strain gauge on the forceps that is operatively connected to a video display or a speaker to produce a human-sensible signal.

Still another aspect of the invention provides mechanical break-away means that utilizes a spring-biased detent member on the break-away joint that disengages when the component of force exceeds the predetermined level, while still another provides electrical break-away means that utilizes a strain gauge on the forceps for producing an electrical signal indicative of when the magnitude of the component of force exceeds the predetermined level. The electrical signal is used to activate a solenoid on the forceps that disengages a detent member on the break-away joint and it may also be used to provide a human-sensible signal when the detent disengages.

Although various force measuring arrangements exist in the prior art for use with forceps, many measure the appositional force applied to an object being gripped (i.e., the force along a line extending between the tips) instead of the pulling force applied to the object generally perpendicular to the appositional force. Also, such existing force measuring arrangements do not provide a means of automatically responding when a predetermined force level is reached. In other words, they measure force, but they do not automatically break away to limit the pulling force applied to an object.

In addition, existing force measuring arrangements may not be sensitive enough to be useful in such work as suturing the cornea where force increments of two-tenths of a gram or less may be important. Furthermore, the existing force measuring arrangements are subject to an inverse relationship between sensitivity and mechanical stability. Moreover, the surgeon may use an operating microscope in cataract and corneal surgery so that it is not feasible to divert attention from the microscopic operative field to read force-measuring calibrations, nor is it desirable to use a large or unwieldy forceps.

Another limitation of the prior art is that there is a trade-off between sensitivity and the structural stability of the arm section. At some level of sensitivity, the required thinness of the arms makes them easily deformed Scott, et al. reported a sensitivity of 0.2 mm/gram with forceps utilizing arms of 0.25 mm thickness where the reference markings were in millimeters. This provides a resolution of no more than about +/−5 grams. To be useful in determining the tension in sutures of the cornea following cataract surgery or corneal transplantation, an instrument should have a resolution of about 0.2 grams or less. In any event, the prior art may suffer the limitation of being subject to a direct inverse relationship between sensitivity (requiring thin arms) and mechanical stability (enhanced by thicker arms).

Yet another limitation in existing forceps is the physical unwieldiness which results from the attachment of a calibrated piece at the proximal end. During microsurgery, space is rather limited and a more compact device would be preferable.

This invention overcomes these concerns with the various inventive aspects mentioned above. Those and other objects and features of the invention and the manner of attaining them will become apparent, and the invention itself will be best understood, by reference to the following description taken in conjunction with the accompanying illustrative drawings.

BRIEF DESCRIPTION OF THE DRAWINGS

FIG. 4 is a perspective view of a second embodiment of a forceps constructed according to the invention;

FIG. 5 is an enlarged sagittal section (cross-sectional side view) of the first or break-away joint of the second embodiment with portions in cross section, the top of FIG. 5 being the top of the forceps;

FIG. 6 is an enlarged coronal section (a cut-away view from above) of the break-away joint with portions in cross section, the top of FIG. 6 being the left side of the forceps;

FIG. 7 is an enlarged top view of the second joint of the second embodiment with portions in cross section;

FIG. 8 is an enlarged elevation view of the second joint with portions in cross section;

FIG. 9 is a further enlarged cross section taken on line 9—9 of FIG. 8;

DESCRIPTION OF THE PREFERRED EMBODIMENTS

Figure 1:
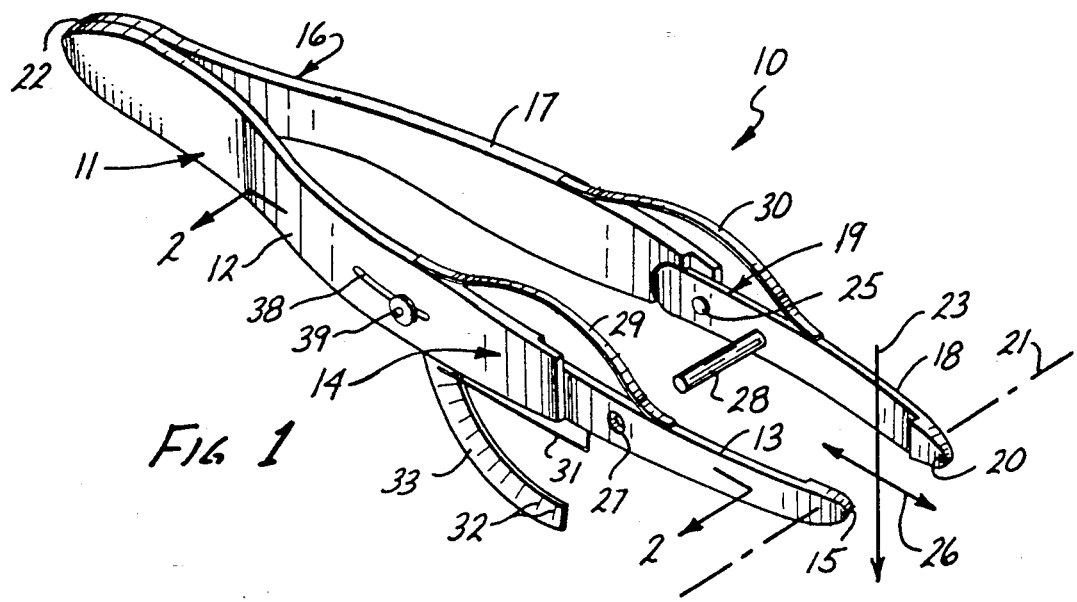
FIG. 1 of the drawings is a perspective view of a first embodiment of a forceps constructed according to the invention.
Figure 2:
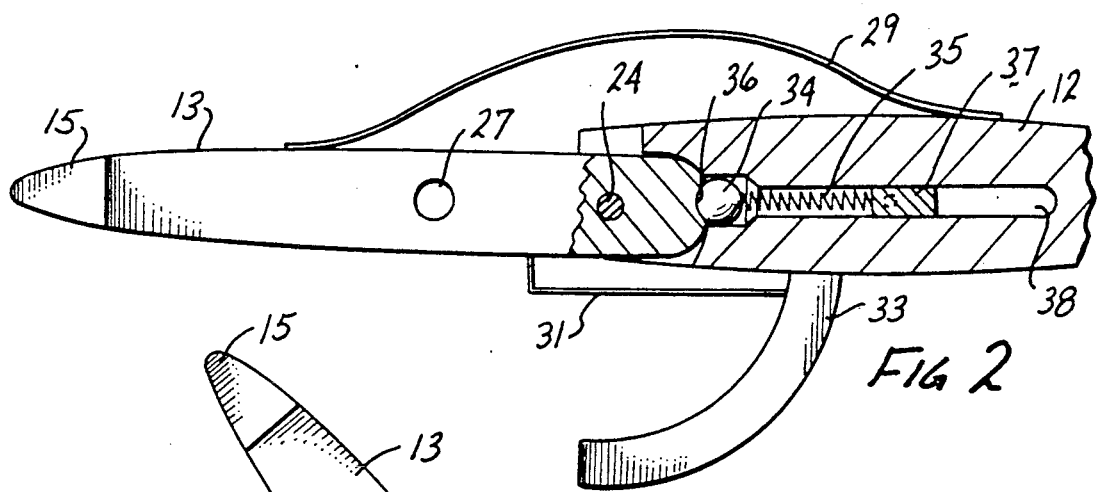
FIG. 2 is an enlarged cross sectional view of a portion of the first embodiment taken on line 2—2 of FIG. 1 showing the distal section in an operative position.
Figure 3:
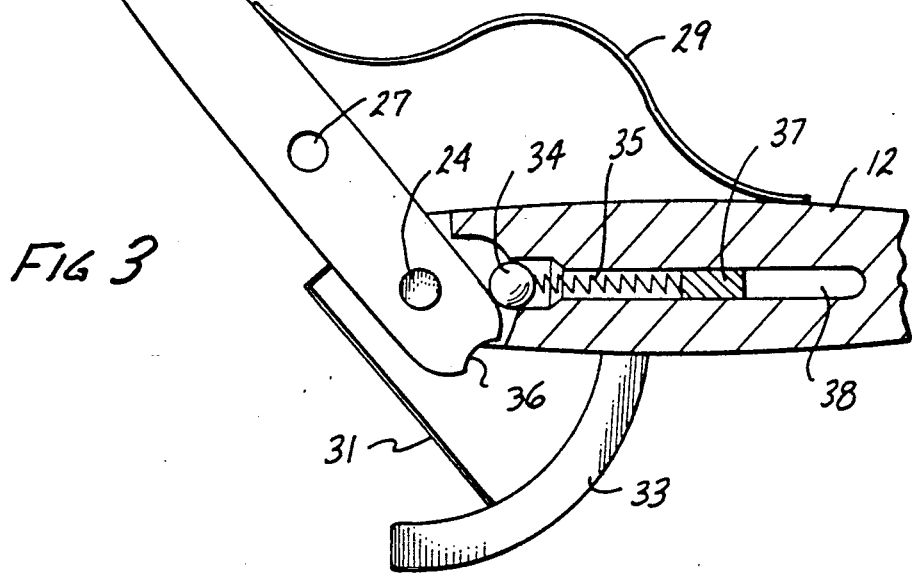
FIG. 3 is a cross sectional view similar to FIG. 2 showing the forceps in a break-away configuration.

Referring now to FIGS. 1-3, there is shown a first embodiment of a surgical forceps 10 constructed according to the invention. It is composed of a suitable material, such as stainless steel, and it is suitably dimensioned and arranged so that it can be grasped with the fingers of a user for purposes of holding and manipulating objects, such as a suture, during various surgical procedures, such as cataract surgery or corneal transplantation. Although the forceps 10 is so arranged, other configurations utilizing different sizes, shapes, and compositions may be employed within the inventive concepts disclosed.

Generally, the forceps 10 includes a first arm 11 having a first proximal section 12 and a first distal section 13 connected with a first joint 14, the first distal section 13 extending to a first forceps tip or first tip 15. The forceps 10 also includes a second arm 16 having a second proximal section 17 and a second distal section 18 connected with a second joint 19, and the second distal section 18 extends to a second forceps tip or second tip 20.

The first and second arms 11 and 16 are arranged and interconnected to enable appositional movement of the first and second tips 15 and 20 toward and away from each other along a direction or line 21 (FIG. 1). In this regard, the first and second arms 11 and 16 are connected at a joint 22 (FIG. 1) and the material of which they are composed is sufficiently resiliently flexible to enable the arms 11 and 16 to be grasped between the fingers of a user and flexed to impart such appositional movement.

This enables a user to grip an object (not shown) between the first and second tips 15 and 20 and thereby apply a component of force to the object that is generally perpendicular to the line 21 (in other words, perpendicular to the direction of such appositional movement). The component of force may be the tension applied to a suture in order to tighten a knot in the suture, or the tension applied to tissue in the eye during surgical procedures, for example.

The first and second joints 14 and 19 couple appositional force from the proximal sections 11 and 16 to the distal sections 13 and 18, and thereby to the tips 15 and 20. This enables a user to grip an object between the tips 15 and 20, the appositional force being applied to the object along the line 21.

The first and second joints 14 and 19 also couple a component of force between the first and second proximal sections 11 and 16 and the first and second distal sections 13 and 18 that is generally perpendicular to the line 21. This enables a user to apply tension to or pull or push on an object being gripped between the first and second tips 15 and 20 in a direction generally perpendicular to the line 21.

Such a component of force 23 is shown in FIG. 1, and the arrowhead indicates the direction the component of force 23 pulls on the object being gripped. The first and second joints 14 and 19 are arranged so that each of the first and second distal sections 13 and 18 can move pivotally relative to a respective one of the first and second proximal sections 12 and 17 (in a direction opposite to that indicated by the arrowhead on the component of force 23).

In this regard, the first distal section 13 pivots about a first pivot pin 24 (FIGS. 2 and 3) that pivotally connects the first distal section 13 to the first proximal section 12. Similarly, the second distal section 18 pivots about a second pivot pin 25 (FIG. 1) that pivotally connects the second distal section 18 to the second proximal section 17.

The component of force 23 is directed along the path the first and second tips 15 and 20 travel when the first and second distal sections 13 and 18 pivot, as opposed to being directed radially toward the pivot pins 24 and 25. Such a radial direction is depicted by a double-headed arrow 26 in FIG. 1 which is perpendicular to both the component of force 23 and the line 21. The component of force 23 may be directed generally perpendicular to both the line 21 and the double-headed arrow 26 by the user appropriately manipulating or applying force to the first and second proximal sections 11 and 17.

Operationally, the user grasps the forceps 10, with the user's fingers placed over the first and second arms 11 and 16, and, if necessary, the user adjusts the first and second distal sections 13 and 18 so that they are in an unpivoted position as subsequently described with reference to FIG. 2. Next, the user advances the first and second tips 15 and 20 to a position such that an object to be gripped (such as a suture) is located intermediate the first and second tips 15 and 20. Then, the user squeezes the first and second arms 11 and 16 in order to cause appositional movement of the first and second tips 15 and 20 toward each other along the line 21, thereby gripping the suture. The user continues to squeeze with sufficient force to grip the suture as tightly as desired.

To apply tension to the suture (in order to tighten a knot, for example), the user continues to squeeze the first and second arms 11 and 16 while applying the component of force 23 to them, the component of force 23 being coupled from the first and second proximal sections 12 and 17 to the first and second distal sections 13 and 18 by the joints 14 and 19, and from there to the suture by the first and second tips 15 and 20.

In the event the component of force 23 exceeds a predetermined value, the first joint 14 breaks away as subsequently described, thereby quickly reducing the magnitude of the component of force applied to the suture. In other words, the first and second distal sections 13 and 18 are free to move substantially relative to the first and second proximal sections 12 and 17 in response to little force. This gives the user a clear indication that the predetermined level has been reached and a brief period of time to readjust the force being applied in order to avoid the prolonged application of too much force to the suture.

In this regard, a hole 27 in the first distal section 13 receives a mating follower pin 28 that is attached to the second distal section 18 when the first and second tips 15 and 20 move toward each other (FIG. 1). This causes the first and second distal sections 13 and 18 to move or pivot together. In other words, this arrangement serves as follower means for causing the second distal section 18 to follow movement of the first distal section 13.

In addition, leaf springs 29 and 30 are provided to lightly spring bias the first and second distal sections 13 and 18 toward the unpivoted position illustrated in FIG. 1. They are composed of a suitable material, such as a metal alloy, and they are attached by suitable known means, such as bonding.

When the first joint breaks away as subsequently described, the leaf springs 29 and 30 determine the force required to pivot the first and second distal sections 13 and 18 out of the unpivoted position. When very little or no force is applied, the leaf springs 29 and 30 cause the first and second distal sections 13 and 18 to return toward the unpivoted position.

FIG. 2 illustrates the first distal section 13 in an unpivoted position, while FIG. 3 illustrates it in a pivoted position. As the first distal section 13 moves to various ones of such positions, a pointer member 31 attached to the first distal section 13 points to graduations 32 on a scale member 33 attached to the first proximal section to indicate the magnitude of the component of force 23 being applied to an object gripped between the first and second tips 15 and 20. The leaf springs 29 and 30, the pointer member 31, and the scale member 33 can all be appropriately configured to mate with graduations 32 that represent two-tenths of a gram or less, for example, and these components may be called pointer-and-graduated-scale means for indicating the relative magnitude of the component of force.

Considering now the break away mechanism in the first joint 14, it includes a detent member 34 that is connected to the first proximal section 12 with a spring 35 (FIGS. 2 and 3), and these components may be called detent means for restricting relative movement of the first proximal section and the first distal section until the component of force exceeds the predetermined level. The detent member 34 may be ball-shaped, for example, and the spring 35 spring biases the detent member 34 toward a mating recess 36 in the first distal section 13 where the detent member 34 seats to restrict relative movement of the first proximal section 12 and the first distal section 13.

The spring 35 is attached to an adjustable keeper 37 that is movably mounted in a slot 38 in the first proximal section 12. A thumb screw arrangement 39 (FIG. 1) locks the keeper 37 in a selected position so that the force the spring 35 exerts on the detent member 34 is sufficient to restrict relative movement of the first proximal section 12 and first distal section 13 until the magnitude of the component of force 23 exceeds the predetermined level.

When the magnitude of the component of force 23 exceeds the predetermined level, the force with which the detent member 34 is held in the recess 36 is overridden so that the detent member 34 cams out of the recess 36. In other words, it disengages so that the first distal section 13 can pivot (i.e. move substantially relative to the first proximal section 12). By operation of the thumbscrew arrangement 39 and positioning of the keeper 37, the user can adjust the magnitude of the component of force 23 that is required for the first joint to break away in this manner.

Considering now the forceps 100 (FIGS. 4-9), it is similar in many respects to the forceps 10 and only differences are described in further detail. For convenience, many of the reference numerals designating features of the forceps 100 are increased by one hundred over those designating similar features of the forceps 10.

Whereas in the forceps 10 the first and second joints 14 and 19 are arranged to enable the first and second distal sections 13 and 18 to move pivotally relative to the first and second proximal sections 12 and 27, the first and second joints 114 and 119 in the forceps 100 are arranged to enable the first and second distal sections 113 and 118 to move linearly relative to the first and second proximal sections 112 and 117.

In this regard, each of the first and second distal sections 113 and 118 is connected telescopically to a respective one of the first and second proximal sections 112 and 117, and this enables relative movement of the proximal and distal sections along the path of the component of force 123 (generally perpendicular to appositional movement of the tips 115 and 120 along the line 121). As a result, operation of the forceps 100 involves the user pulling on the arms 116 and 117 in the direction of the component of force 123.

Further details of the break-away first joint 114 are shown in FIGS. 5 and 6. It includes a covering or sheath 140 composed of a flexible material such as a thermoplastic material that covers a pair of retainer members 141 and 141'. These are attached to the first proximal section 112 by suitable means such as bonding and arranged to extend through holes 142 and 142' in the first proximal section 112 toward the first distal section 113 (FIG. 5).

The retainer members 141 and 141' are generally similar so that only the retainer member 141 is described in further detail. It includes a detent portion 134 and a leaf spring portion 135. The leaf spring portion spring biases the detent portion 134 toward an annular recess 136 in the first distal section 113 where it seats to restrict relative movement of the first proximal section 112 and first distal section 113 until the magnitude of the component of force 123 exceeds a predetermined level.

When the magnitude of the component of force 123 exceeds the predetermined level, the force with which the detent portion 134 is held in the annular recess 136 is overridden so that the detent member 134 cams out of the annular recess 136. In other words, it disengages so that the first distal section 113 can move axially or telescopically out of the first proximal section 112 and in so doing move substantially relative to the first proximal section 112.

The second joint 119 is arranged to enable the second distal section 118 to telescope out of the second proximal section 117 and thereby follow movement of the first distal section 113. Springs 129 and 130 lightly spring bias the first and second distal sections 113 and 118 toward the unextended position that is illustrated in FIGS. 5-9, and a distal edge 131 of the first proximal section 112 cooperates with graduations 132 on the first distal section 113 to serve as pointer-and-graduated-scale means.

Ball bearings 143 and 143' (FIGS. 6 and 8) are provided to facilitate movement of the first and second distal sections 113 and 118, and they are retained in place by O-rings 112' and 117' that also provide a seal between the proximal and distal sections. In addition, the first and second distal sections 113 and 118 are provided with radially extending ears that fit in grooves in the first and second proximal sections 112 and 117 to prevent rotation of the first and second distal sections relative to the first and second proximal sections.

The anti-rotation aspect is illustrated in FIGS. 7-9 for the second distal section 118. Radially extending ears 144 and 145 on the second distal section 118 fit in grooves 146 and 147 in the second proximal section 117 to prevent rotation of the second distal section 118 relative to the second proximal section 117. The first distal section 113 is configured in a similar manner with radially extending ears 144' and 145' that fit in grooves 146' and 147' (FIGS. 5 and 6).

The forceps 100 also includes means for adjusting the amount of force needed to cause the joint 114 to break away. The sheath 140 is threaded onto the first proximal section 112 and a portion 140' of the sheath 140 (FIG. 5) is dimensioned so that it contacts the leaf springs 135 and 135' as the sheath 140 is rotated and advanced distally. This depresses the leaf springs to increase the force needed to cam the detent portions 134 and 134' out of the annular recess 136.

Thus, by rotating the sheath 140 to a desired position as indicated by the position of calibrating marks 148 relative to reference mark 149 (FIG. 4), the surgeon can adjust the magnitude of the force 123 needed to break away the joint 114. In other words, the calibrating marks 148 cooperate with reference mark 149 to indicate the magnitude of the component of force 123 required to cause the joint to break away.

Figure 10:
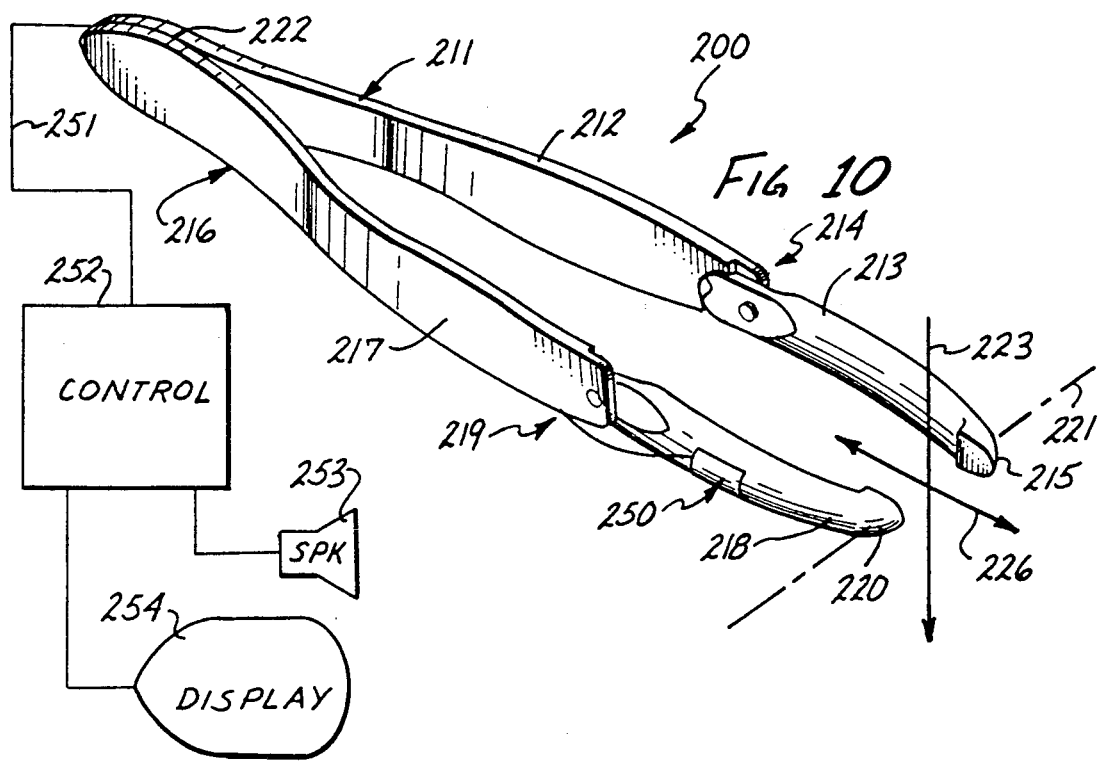
FIG. 10 is a perspective view of a third embodiment of a forceps constructed according to the invention, including electronic components shown diagrammatically.
Figure 11:
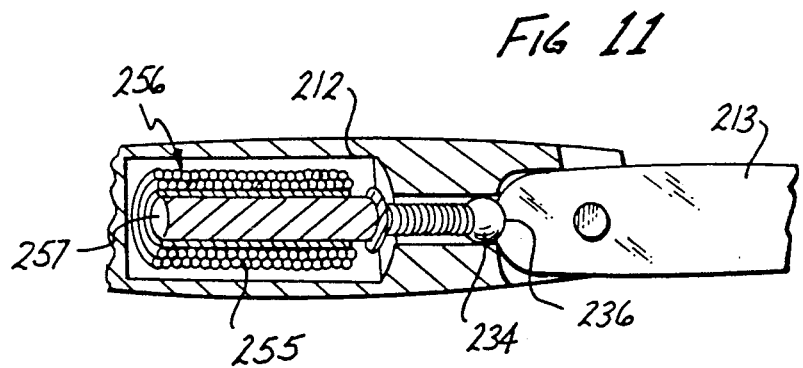
FIG. 11 is an enlarged elevation view of the first or break-away joint of the third embodiment with portions in cross section.
Figure 12:
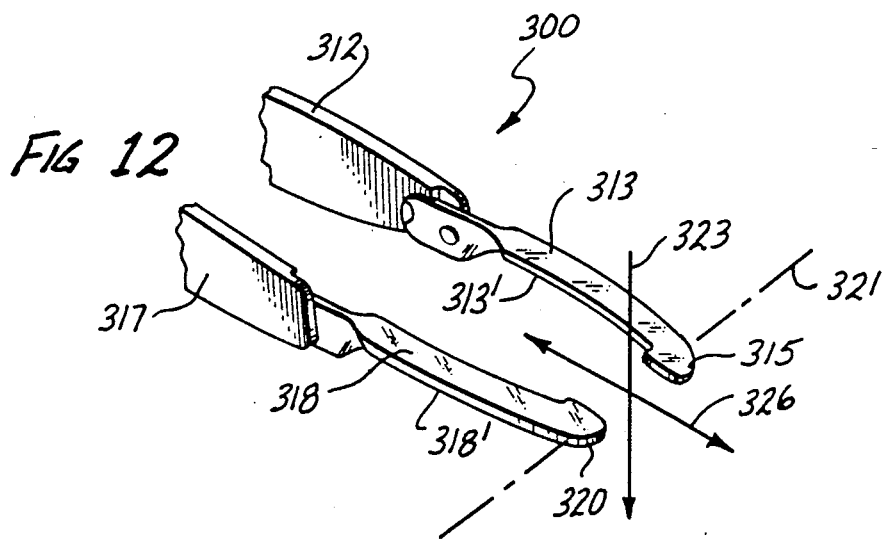
FIG. 12 is a perspective view of the distal sections of a fourth embodiment of the invention.

Considering now the forceps 200 (FIGS. 10 and 11, it is also similar in many respects to the forceps 10 and only differences are described in further detail. For convenience, many of the reference numerals designating features of the forceps 200 are increased by two hundred over those designating similar features of the forceps 10.

Although the forceps 200 includes first and second joints 214 and 219 that enable pivotal movement similar to that of the forceps 10, the break-away scheme is electrical instead of mechanical. A known type of strain gauge arrangement 250 is attached to the second distal section 218 (FIG. 10) according to known techniques to produce an electrical signal indicative of the relative magnitude of the component of force 223 applied to an object being gripped between the first and second tips 215 and 220. The strain gauge arrangement 250 may employ resistive elements in a Wheatstone bridge configuration, for example.

The electrical signal is coupled by a line 251 to suitable electrical control circuitry 252 where it is processed according to known techniques and utilized to produce a human-sensible signal, such as a variable-frequency audible tone over a speaker 253 or a visually-discernible display on a display device 254.

The control circuitry 252 may be configured according to known techniques to produce a control signal as well when the magnitude of the component of force exceeds a predetermined level. This control signal is transmitted over the line 251 back to break-away components in the first joint 214.

The joint 214 includes a detent member 234 (FIG. 11) that seats in a recess 236 in the first distal section 213 in order to restrict relative movement of the first proximal section 212 and first distal section 213. The control signal is coupled to a solenoid coil 255 of a solenoid 256 that is located in the first proximal section 112, and this energizes the solenoid 256 to cause a plunger 257 of the solenoid to withdraw the detent member 234 from the recess 236. This, in turn, enables substantial relative movement of the proximal and distal sections to quickly reduce the magnitude of the component of force 223 being applied. It quickly decouples the first distal section 213 from the first proximal section 212.

The forceps 300 employs electrical break-away components as well (not shown), but the first and second distal sections 313 and 318 are configured differently from the first and second distal sections 213 and 218 of the forceps 200. The first and second distal sections 313 and 318 are thicker and more rigid in the direction of appositional movement (line 321), and they are thinner and less rigid in the direction of the component of force 323.

A known type of strain gauge arrangement (not shown) is fastened to each of the first and second distal sections 313 and 318. The strain gauge is bonded or otherwise suitably attached to the undersides of the broad, flat first and second distal sections 313 and 318 (the bottom surfaces 313' and 318' in FIG. 112). Summing currents through the resistors according to known techniques improves signal-to-noise characteristics to facilitate production of an electrical signal indicative of the relative magnitude of the component of force 323. The forceps 300 is otherwise generally similar to the forceps 200.

Thus, this invention in its various forms provides a surgical forceps with break-away, force-measuring, and related features that overcome many problems of the prior art. Although described in conjunction with suturing during cataract and corneal surgery, it is intended that the scope of the claims not be so limited. It is intended that the scope of the claims extend to any of various other uses.

Although an exemplary embodiment of the invention has been shown and described, many changes, modifications, and substitutions may be made by one having ordinary skill in the art without necessarily departing from the spirit and scope of the invention.

What is claimed is:

1. A forceps comprising:
a first elongated arm having a first proximal section and a first distal section, the first distal section having a first tip;
a second elongated arm having a second proximal section and a second distal section, the second distal section having a second tip;
means for interconnecting the first and second arms with the first and second tips being movable along a path to grip an object;
said first and second arms when gripping the object being usable to apply a component of force to the object that is generally perpendicular to said path;
a first joint for coupling the first proximal section to the first distal section so that the component of force with a magnitude up to a predetermined level can be transmitted from the first distal section to the first proximal section; and
the first joint including break-away means responsive to the component of force exceeding said predetermined level for quickly and automatically reducing the magnitude of the component of force that can be transmitted by the first joint to a magnitude less than the predetermined level.

2. A forceps as recited in claim 1, wherein:
the first joint is arranged to enable relative movement of the first proximal section and the first distal section; and
the break-away means includes detent means for restricting relative movement of the first proximal section and the first distal section until the component of force exceeds the predetermined level.

3. A forceps as recited in claim 2, wherein:
the second proximal section and the second distal section are joined together with a second joint that enables relative movement of the second proximal section and the second distal section; and
means for causing the second distal section to follow movement of the first distal section.

4. A forceps as recited in claim 1, further comprising:
means for indicating the magnitude of the component of force.

5. A forceps as recited in claim 4, wherein the means for indicating includes:
strain gauge means for producing an electrical signal indicative of the magnitude of the component of force.

6. A forceps as recited in claim 4, wherein the means for indicating includes:
pointer-and-graduated-scale means for indicating the relative magnitude of the component of force.

7. A forceps as recited in claim 1, wherein:
the first joint enables the first distal section to move pivotally relative to the first proximal section.

8. A forceps as recited in claim 1, wherein:
the first joint enables the first distal section to move linearly relative to the first proximal section.

9. A forceps as recited in claim 8, wherein:
the first and second proximal sections are connected telescopically to respective ones of the first and second distal sections.

10. A forceps as recited in claim 1, wherein the break-away means includes:
mechanical break-away means.

11. A forceps as recited in claim 1, wherein the break-away means includes:
electrical break-away means.

12. A forceps as recited in claim 11, wherein the electrical break-away means includes:
strain gauge means for producing an electrical signal indicative of the magnitude of the component of force; and
means responsive to the electrical signal for quickly reducing the coupling of the component of force when the component of force exceeds the predetermined level.

13. A forceps as recited in claim 12, wherein:
the first joint is arranged to enable relative movement of the first proximal section and the first distal section; and
the break-away means includes detent means for restricting relative movement of the first proximal section and the first distal section; and
the means responsive to the electrical signal includes solenoid means for disengaging the detent means.

14. A forceps as defined in claim 1 wherein the first and second arms are elongated and the component of force is generally perpendicular to the direction of elongation of the arms.

15. A forceps as defined in claim 1 wherein the first and second arms are elongated and the component of force is generally in the direction of elongation of the first and second arms.

16. A forceps comprising:
a first elongated arm having a first tip;
a second elongated arm having a second tip;
means for interconnecting the first and second arms for movement of the tips in a first direction toward each other so that the tips can grip an object and a component of force can be applied to the object in a second direction which is generally perpendicular to said first direction; and
said arms including means responsive to the component of force exceeding a predetermined level for automatically allowing said first and second tips to move in said second direction.

17. A forceps as defined in claim 16 wherein said second direction is generally perpendicular to the direction of elongation of the arms.

18. A forceps as defined in claim 16 wherein said second direction is generally in the direction of elongation of said arms.

* * * * *